| United States Patent [19] | [11] | 4,195,083 |
|---|---|---|
| Hoy et al. | [45] | Mar. 25, 1980 |

[54] VETERINARY COMPOSITIONS AND METHOD FOR CONTROLLING ANTHROPOD ECTOPARASITES

[76] Inventors: John Hoy, 32 Becker St.; Gordon N. Emby, 16 Myrtle Ave. Post Office North Rand, both of, Johannesburg, Transvaal; Edgar F. Meerholz, 22 Gloucester Ave., Sandringham, Johannesburg, Transvaal, all of South Africa

[21] Appl. No.: 913,353

[22] Filed: Jun. 7, 1978

Related U.S. Application Data

[63] Continuation of Ser. No. 569,674, Apr. 21, 1975, abandoned, which is a continuation of Ser. No. 284,404, Aug. 28, 1972, abandoned, which is a continuation-in-part of Ser. No. 855,556, Sep. 5, 1969, abandoned.

[30] Foreign Application Priority Data

Sep. 11, 1968 [ZA] South Africa .......................... 685864

[51] Int. Cl.$^2$ ................. A61K 31/675; A61K 31/665; A61K 31/66
[52] U.S. Cl. ..................................... 424/200; 424/203; 424/205; 424/212; 424/215; 424/218; 424/219; 424/225
[58] Field of Search ............... 424/212, 219, 203, 205, 424/225, 200, 215, 218

[56] References Cited

U.S. PATENT DOCUMENTS

| 2,611,729 | 9/1952 | Bartlett et al. . |
|---|---|---|
| 3,065,125 | 11/1962 | Newallis et al. . |

FOREIGN PATENT DOCUMENTS 240255  5/1960  Australia .

OTHER PUBLICATIONS

Medley et al., J. of Economic Entomology, vol. 56 (1963) pp. 658–660.
Smith et al., J. of Economic Entomology, vol. 48 (1955) pp. 566–568.
Moore et al., J. of Economic Entomology, vol. 52 (1959) pp. 980–981.

*Primary Examiner*—Sam Rosen
*Attorney, Agent, or Firm*—DeLio and Montgomery

[57] ABSTRACT

A self-emulsifiable liquid pesticidal concentrate comprising: (a) from 65 to 95 percent by weight of a liquid pesticide compound or a liquid mixture of a liquid pesticide compound and a solid pesticide compound, (b) an emulsifier, and (c) 0% to 10% by weight of a solvent for the pesticide compound. In the method of application the pesticide concentrate is mixed with water so that a pesticidal emulsion dip is formed, having a total pesticide compound content of from 0.005 to 0.5 parts by weight per 100 parts by volume of emulsion. An animal infested with arthropod ectoparasites is treated with the pesticidal emulsion dip to eliminate and protect the animal from these parasites.

8 Claims, 4 Drawing Figures

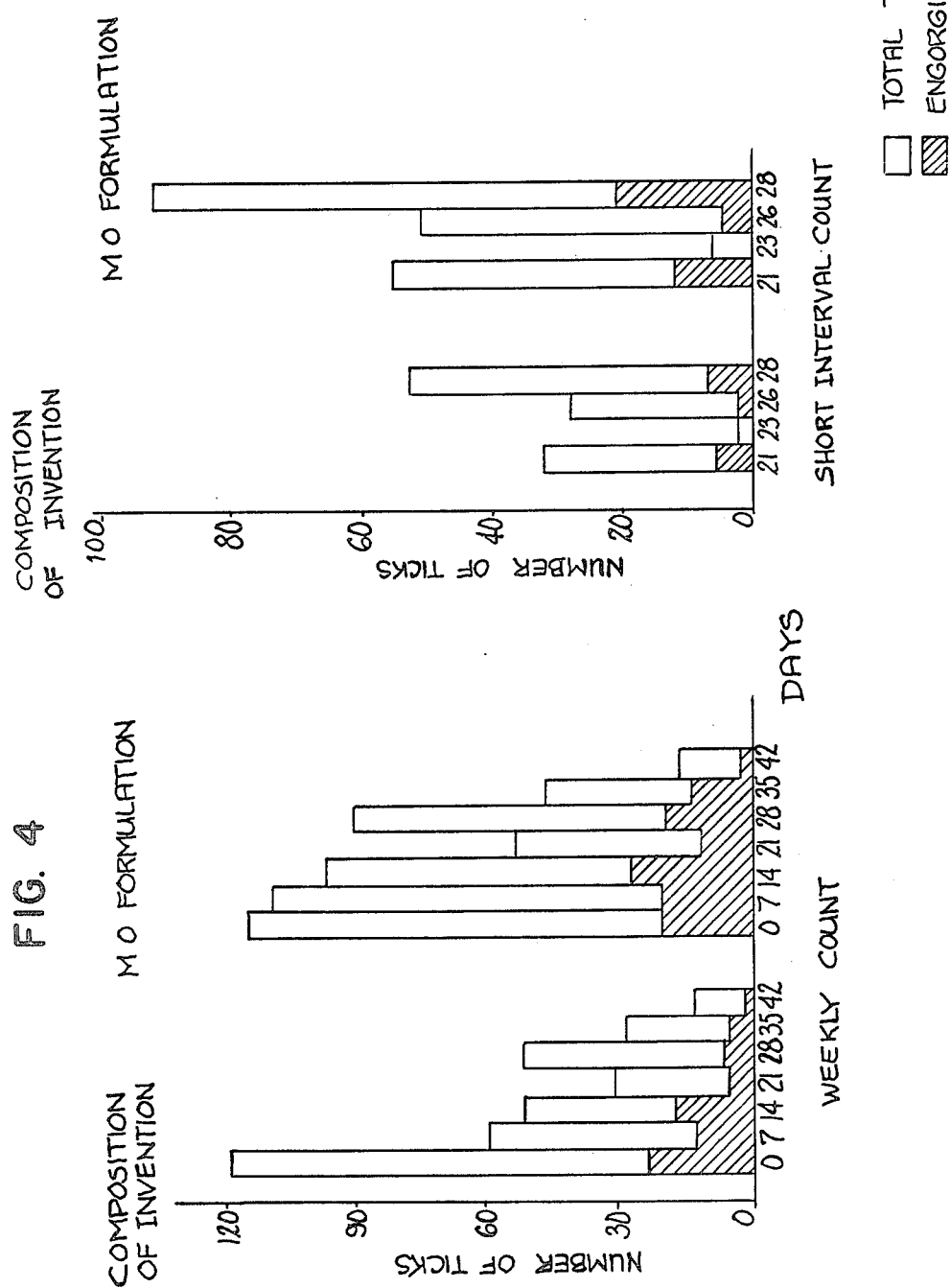

VETERINARY COMPOSITIONS AND METHOD FOR CONTROLLING ANTHROPOD ECTOPARASITES

CROSS-REFERENCE TO RELATED APPLICATION

This application is a continuation, of application Ser. No. 569,674, filed Apr. 21, 1975. Ser. No. 569,674 is a continuation of Ser. No. 284,404, filed Aug. 28, 1972. Ser. No. 284,404 is a continuation-in-part of Ser. No. 855,556, filed Sept. 5, 1969, all now abandoned.

This invention relates to pesticidal compositions, their preparation and their use in controlling ectoparasites of mammals. In particular, it relates to non-aqueous, self-emulsifiable, solvent-free, pesticidal compositions containing a substantial quantity of a pesticides as the active ingredient.

In most parts of the world, domesticated mammals including livestock, are subject to infestations by external parasites. The most important class of such parasites are anthroped ectoparasites especially those belonging to the class Inseeta and the order Acarina. These pests include lice, flies, ticks and mites which are often not only injurious to the host-mammals themselves, but are vectors of disease-causing organisms and cause substantial financial losses to livestock farmers. Estimates of the losses caused by the more important pests affecting livestock production are given in a Report issued by the U.S. Department of Agriculture (Agricultural Handbook 291), from which it will be noted that the losses can amount to millions of U.S. dollars per annum.

Among pests of significant economic importance is *Boophilus decoloratus,* a tick mainly affecting cattle and equines in Africa south of the Sahara, which is a vector of a number if diseases including anaplasmosis and babesiosis in cattle. Another tick prevalent in Africa is the "brown ear tick", *Rhipicephalus appendiculatus* Neumann, which is parasitic on cattle, equines, sheep, goats and other mammals. It is the chief vector of East Coast fever of cattle and is implicated in the transmission of other diseases as well. These are of course many other ectoparasites of domesticated animals among which may be briefly mentioned *Rhipicephalus evortsi* and *Amblyoma lobracm* parasitic on sheep and cattle; *Lucilia cuprin* and sericata parasites on sheep; and *Chrysoxyia bezziana* (screw worm) parasitic on cattle, sheep and and goats. All such ectoparasites are to a greater or lesser extent responsible for economic losses which can take the form of decreased meat, milk, and wool production, damaged hides, general debilitation and even the death in cases of heavily parasitised animals.

At present, the major practical means for controlling such anthropod ectoporasites is by the use of chemicals toxic to these parasites. Among a large variety of such chemicals - or pesticides - which have been used for this purpose are the organo-phosphorous and the organo-chlorine pesticides. These are relatively insoluble in water and are presented for use in the field as dips which are usually in the form of wettable powders or miscible oils (also known as emulsifiable concentrates). The miscible oil formulations contain solvents and emulsifiers and are applied to the infested animals as an emulsion in water which is prepared by diluting the formulations to provide the desired concentration of active ingredient. These emulsions are known as washes and are applied to the animals by spraying (spray washes) or by dipping or immersing the animals in the wash (dip wash). Applications of the pesticide in this way reduces or eliminates the infestation and provides some degree of protection against re-infestation.

Dipping in and spraying with emulsion washes is extensively practised in Africa, Europe, the Americas and Australasia. A cattle dipping bath, for example, may hold at least 3,000 gallons of dip wash in which cattle are successively dipped. Each animal removes several gallons of wash from the bath, but most of this returns to the bath via the draining pens. An additional amount of the pesticide is, however, selectively adsorbed by the hair or skin of the animal which leads to a progressive decrease in the concentration of the wash as more animals are dipped in the same wash. This decrease is known as "stripping", "exhaustion" or "depletion" of the wash, and is undesirable in view of the necessity of continually checking the concentration of the wash and the need for replenishment.

The conventional miscible oil formulations of liquid pesticides used to prepare washes are characterized by the presence of a high solvent content for the active ingredient which may be as much as 80 percent by weight of the formulation. It is usually in the range of 50 to 70 percent by weight but rarely falls below 30 to 40 percent by weight. Another feature of these conventional formulations is the relatively low concentration of the pesticide which rarely exceeds 55 percent by weight and is usually in the range of 2 to 30 percent by weight of the composition. Apart from the active ingredient, other substances, termed in the art together with the solvents referred to above as "inerts", are commonly included to reduce the viscosity, to stabilize or to dilute the conventional miscible oil compositions.

The inclusion of a solvent in these conventional miscible oil formulations has been established practice for many years (see for example U.K. Pat. Specification No. 1,144,003, page 3, lines 72 to 102). Apart from acting as a solvent for the active ingredient, its inclusion was especially believed to be of value in reducing the rate of "exhaustion" of a dip or spray wash made from a formulation. It was thus shown by Brown, et al ("The formulation of Pesticides"; S.C.I. Konograph No. 21, Society of Chemical Industry, 1966, at pages 166 to 172) that the more solvent present in the dip (and hence in the wash), the lower the degree of exhaustion. It was also feared that the omission of a solvent would produce dips which would be more toxic to handle in view of high concentration of the active ingredient. In consequence it has been the invariable practice for many years to include a substantial amount of a solvent in miscible oil formulations.

It has been surprisingly found , contrary to established opinion and accepted practice in making miscible oil formulations of liquid pesticides, that it is not necessary to include a solvent; that a satisfactory dip can be made without the inclusion of such solvents; that the presence of a solvent in substantial amounts can have deleterious effects on mammals; and that dip washes made from such solvent-free dips have improved biological effects and do not exhaust to a substantially greater extent than dips made from conventional formulations containing a solvent.

Accordingly the present invention provides a method for the control of arthropod ectoparasites of mammals using an emulsion in water of a self-emulsifiable, substantially solvent-free (as hereinafter defined), non-aqueous, pesticidal composition comprising at least one liquid pesticide and an emulsifier, which composition has a total pesticide content of from 65 to 95 percent by weight of the composition. There is also provided by this invention a dip which comprises a composition as defined above; and a container marked with indications of substantially of its contents for the control of arthrapod ectoparasites of mammals, the said contents being a composition as defined above.

The following figures graphically depict the results of tests on cattle in which.

Figure 1:
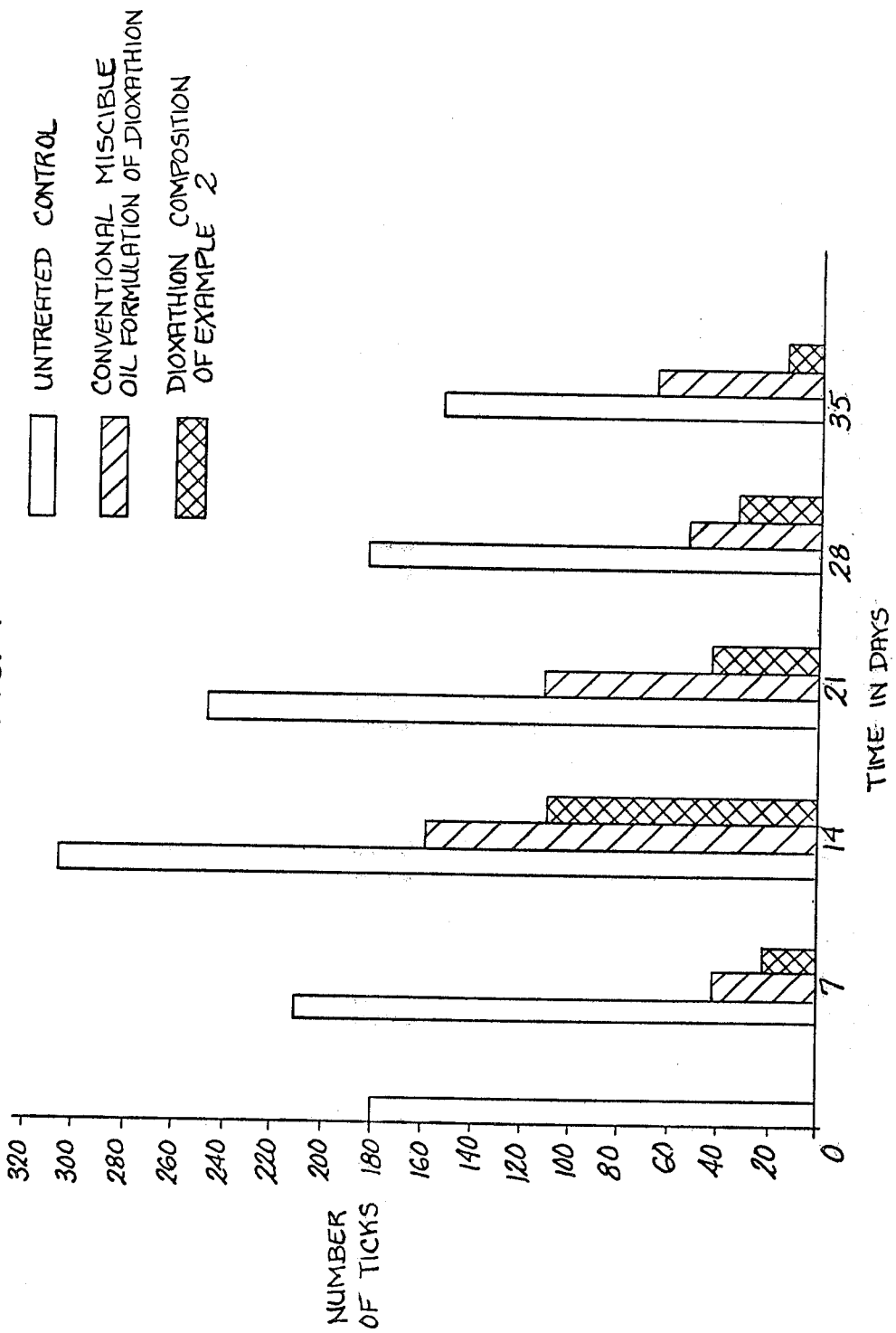
FIG. 1 is a graph showing comparative infestation of ticks in point of time in accordance with the trial tests referred to in Example 6.

A pesticide for use in the compositions may be any pesticide which is liquid at normal ambient temperatures, and is suitable for veterinary use; that is to say, suitable for the control of arthropod ectoparasites of mammals. Organo-phosphorous pesticides of the phosphate and phosphorothionate ester type are especially preferred and include such chemicals as chlorfenvinphos (2-chloro-1(2,4-dichlorophenyl) vinyl diethyl phosphate), ethion (O,O,O',O'-tetraethyl S,S'-methylenediphosphorodithioate), dioxathion [2,3-p-dioxanedithiol S,S-bis(O,O-diethyl phosphorodithionate)], 'Diazinon' (Trade Mark) (O,O-diethyl-O-2-isopropyl-4-methyl-6-pyrimidyl phosphorothionate), dichlofenthion (O,O-diethyl O-2,4-dichlorophenyl phosphorothionate), carbophenthion (O,O-diethyl S-(p-chlorophenylthio) methyl phosphorodithioate), bromophos ethyl (O,O-diethyl O,4-bromo-25,-dichlorophenyl phosphorothionate), folithion (O,O-dimethyl O-(3-methyl-4-nitrophenyl) phosphorothionate), dibrom (O,O-dimethyl O-1,2-dibrono-2,2-dichloroethyl phosphate), and fenthion (dimethyl 3-methyl-4-methylthiophenyl phosphorothionate). Mixtures of two or more of these pesticides may, if desired, be included in the compositions. A solid pesticide may also be included in the compositions in addition to one or more liquid pesticides, and 'Dursban' (Trade Mark) (O,O-diethyl O-3,5,6-trichloro-2-pyridylphosphorothionate is usefully included in combination with bromophos ethyl. Other solid pesticides which may be used include fenchlorphos (O,O-dimethyl O-(2,4,5-trichlorophenyl) phosphorothionate) and 'Imidan' (Trade Mark) (N-(mercaptomethyl)-phthalimido S-(O,O-diemthyl phosphorodithioate)).

The pesticide content of a composition is conveniently not less than 75 percent by weight of the composition, and the preferred content will vary with the nature of the pesticide chosen, and the nature and quantity of the remaining ingredients.

The emulsifier for inclusion in a composition may be any emulsifier which is miscible with the liquid insecticide and provides a satisfactory emulsion of the composition in water. The emulsifier may constitute the sole additional ingredient with the pesticide and thus make up the balance of 5 percent to 35 percent by weight of the composition, or further ingredients may be included, as described below. The preferred emulsifiers are non-ionic or anionic surface active agents having emulsifying and dispersing properties, and a blend (or mixture) of these two types is especially useful for compositions of the invention.

Suitable non-ionic surface active agents include polyalkylene glycol ethers, and condensation products of alkyl phenols, aliphatic alcohols, aliphatic amines or fatty acids with ethylene oxide. Conveniently the emulsifier may be a condensation product of nonyl phenol with 5 to 25 mols. of ethylene oxide, mixed with a polyalkylene glycol. Anionic surface active agents which may be used include calcium salts of alkylbenzene sulphonic acids, naphthalene sulphonic acid, and salts of lauryl sulphate.

Although the compositions of the invention are non-aqueous in character, that is to say, they contain no added water, it is commonly found that surface active agents usually employed in the manufacture of pesticidal compositions contain up to about 3 percent by weight of water. Compositions containing much surface active agents are therefore also included within the scope of the present invention.

Further substances may be included in compositions of the present invention, in addition to the pesticide and emulsifier, in order to supplement the activity of the composition or to modify its properties. Such substances should be miscible with the remaining ingredients of the composition and include bactericides, bacteriostats, fungicides, corrosion inhibitors, perfumes, diluents and viscosity reducing agents.

Although it is a main object of the present invention to provide compositions not containing any solvent for the purpose of solubilising the pesticide ingredient, such solvents may be included in compositions of the invention in an amount not exceeding 10 percent and preferably not more than 5 percent by weight of the composition for the purpose of reducing viscosity or adjusting the concentration of the pesticide to provide a desired concentration in a wash on dilution. In this specification "solvent" means a free-flowing organic liquid of low viscosity which is readily miscible with the remaining ingredients of a composition, and includes such substances as hydrocarbon solvents, for example alkyl benzenes, alkyl naphthalenes, xylone, paraffins, aliphatic alcohols, and ethers commonly employed in solubilising the active ingredient of pesticidal compositions. The inclusion of a small amount of such a solvent as described herein may be useful in preventing the crystallisation of the pesticide in a composition if it should be stored in low temperature climatic conditions. It will therefore be understood that a composition described herein is termed "substantially solvent-free" if its solvent content does not exceed 10 percent by weight of the composition.

A stabiliser for the pesticide may also be included in an amount of from 0.5 to 5 percent by weight of the composition. Suitable stabilisers for organo-phosphorus compounds include propylene oxide, epichlorhydrin and alkanolamines such as triethanolamine.

The compositions of the present invention may be made by intimately admixing the ingredients thereof to produce a uniform composition. If a solid pesticide is included, then this should be first dissolved in the liquid pesticide. If an anionic and non-ionic emulsifier mixture is used, this should be first prepared before the addition of the pesticides.

A wash for the spraying or dipping of infested animals is prepared by adding the composition to water, and dispersing it until an aqueous emulsion of uniform composition is produced. It is preferred, however, to 'precream' the composition, namely to mix the composition with the same amount of water, stirring continuously, to make a highly concentrated emulsion. The stirring is continued and water added to form a thin cream, and this is then added to the remaining quantity of water, with stirring, to provide the desired concentration of pesticide in the wash. It is preferred that in the wash, the particles of the emulsion should be less than 1μ. The optimum concentration of active ingredient in the wash will of course depend upon the nature of the pesticide and its intended use. In general a range of concentration from 0.005% w/v to 0.5% w/v may be used, although most pesticides may be used at a concentration of 0.005% to 0.2% w/v.

The washes made from compositions of this invention may be applied to infected animals by conventional methods, and may be done by dipping the animals in a bath of the wash or spraying the animals with the wash.

The following examples are given to illustrate suitable compositions of the invention and the results obtained in using these compositions in laboratory and field trials, but without limiting the scope of the invention in any way.

Examples 1 to 4 are examples of suitable compositions prepared according to the invention. The ingredients are given in percentages by weight of the total composition in each example.

The remaining examples illustrate the use of the compositions and the results obtained from tests using these compositions.

EXAMPLE 1

A composition was prepared from the following ingredients:

| | |
|---|---|
| Chlorfenvinphos (technical grade) | 87.20 |
| Calcium dodecyl benzene sulphonate (anionic emusifier; technical grade 70% w/w) | 3.84 |
| A non-ionic emulsifier blend: (a mixture of polyalkylene glycol ether; and a condensate of nonylphenol with 10 to 20 mol. ethylene oxide) | 8.96 |

The polyalkylene glycol was molted by gentle heat and mixed with the remaining emulsifiers. The resulting mixture was then added to the insecticide and stirred until an homogenous composition was obtained.

EXAMPLE 2

A composition was prepared from the following ingredients in the manner described in Example 1:

| | |
|---|---|
| Dioxathion (technical grade) | 82.64 |
| Calcium dodecyl benzene sulphonate (anionic emulsifier; technical grade 70% w/w) | 5.20 |
| A non-ionic emulsifier blend: (a mixture of polyalkylene glycol ether; and a condensate of nonylphenol with 10 to 20 mol. ethylene oxide) | 12.16 |

EXAMPLE 3

A composition was prepared in the manner described in Example 1 from the following ingredients:

| | |
|---|---|
| Chlorfenvinphos (technical grade) | 40.24 |
| Dioxathion (technical grade) | 40.24 |
| Calcium dodecyl benzene sulphonate (anionic emulsifier; technical grade 70% w/w) | 5.90 |
| A non-ionic emulsifier blend: (a mixture of polyalkylene glycol ether; and a condensate of nonylphenol with 10 to 20 mol. ethylene oxide) | 13.62 |

EXAMPLE 4

A composition was prepared from the following ingredients:

| | |
|---|---|
| O,O-diethyl O-3,5,6-trichloro-2-pyridylphenphorothionate (technical grade) | 15.0 |
| Bromophos ethyl (technical grade) | 70.0 |
| "Toximal" MPS (Trade Mark) | 15.0 |

The solid insecticide (the pyridylphosphorothionate ester) was dissolved in the liquid insecticide (bromophos ethyl). The emulsifier was added to the mixture and the product stirred to give a homogenous composition.

"Toximul" MP6 is a liquid sulphonate non-ionic blend emulsifier available from Stepen Chemical Co., Illinois, U.S.A.

EXAMPLE 5

The biological activity of the compositions according to the invention against cattle tick larvae was determined by the method described by R. D. Shaw in the Bulletin of Patomological Research, Vol. 56, Part 3, June 1966. The larvae were of the organo-phosphorous-resistant strain (Berlin strain) of *Boophilus decoloratus*. The results were obtained in terms of the larval LC 50 (%), that is, the lowest concentration of active ingredient giving a 50 percent mortality of the larvae. The results are shown in Table 1 together with the results obtained using conventional miscible oil formulations containing the same active ingredients. These conventional formulations contained the following ingredients:

| Dioxathion miscible oil formulation | % w/w |
|---|---|
| Dioxathion (technical grade) | 29.6 |
| Anionic emulsifier | 4.9 |
| Blend of two non-ionic emulsifiers | 4.9 |
| Organic solvent (containing a high proportion of aromatic hydrocarbon) | 60.6 |
| Chlorfenvinphos miscible oil formulation | |
| Chlorfenvinphos (technical grade) | 27.9 |
| Anionic emulsifier | 2.0 |
| Blend of two non-ionic emulsifiers | 6.5 |
| Organic solvent (containing a high proportion of aromatic hydrocarbons) | 62.8 |
| Dioxathion/chlorfenvinphos miscible oil formulation | |
| Dioxathion (technical grade) | 14.1 |
| Chlorfenvinphos (technical grade) | 14.1 |
| Anionic emulsifier | 2.8 |
| Blend of two non-ionic emulsifiers | 6.5 |
| Stabiliser (based on propylene oxide) | 0.8 |
| Organic solvent (containing a high proportion of aromatic hydrocarbons) | 61.6 |

TABLE I

| Formulation or composition | IC 50 (%) |
|---|---|
| Composition of Example 1 | 0.0027 |

TABLE I-continued

| Formulation or composition | IC 50 (%) |
|---|---|
| Chlorfenvinphos miscible oil formulation | 0.0030 |
| Composition of Example 2 | 0.0011 |
| Dioxathion miscible oil formulation | 0.0028 |
| Composition of Example 3 | 0.0022 |
| Dioxathion/chlorfenvinphos miscible oil formulation | 0.0028 |

These results show that the compositions of the invention have greater pesticidal activity than the corresponding conventional miscible oil formulations containing a solvent.

EXAMPLE 6

The biological efficacy of the dioxathion composition of Example 2 was compared with that of a conventional miscible oil formulation of dioxathion (described in Example 5) in field trials with cattle. The methiod used was that described by J. A. F. Baker and G. E. Thompson in the Journal of the South African Veterinary Medical Association, Vol. 37, No. 3, 1966, pp. 367–372, against *Rhipicephalus appendiculatus* (Brown Ear Tick). The composition and the formulation were each diluted with water to prepare washes containing 0.05% w/v of active ingredient.

The results of these trials are represented in FIG. 1.

The number of ticks is the average number per animal. Each figure was obtained from a group of 3 animals. Treatment of the animals was at weekly intervals and on treatment days, tick mumbers were counted before each treatment.

These results show that the counts on the animals treated with the composition of Example 2 are consistently lower than the counts on the animals treated with the conventional miscible oil formulation.

Statistical analysis of variance on these data showed that the control of ticks using the composition of Example 2 was significantly better than the control with the conventional miscible oil formulation.

EXAMPLE 7

A further comparative field trial with cattle, using the dioxathien composition of Example 2 and a conventional miscible oil formulation of dioxathion described in Example 5, was conducted. The method used was that described in Example 6 to test control of the ectoparasite *Rhipicephalus evortsi* (Neumann) (Red Tick). The composition and the formulation were each diluted with water to prepare washes containing 0.5% w/v of active ingredient.

The animals, divided into two groups of three animals, were treated on day 0 and day 7, total adult tick counts being made just prior to treatment.

In this trial, short interval counts were carried out on days 3, 4, 5, 6 and 7 after the first treatment and on days 10, 11, 12 and 14 after the second treatment (on day 7).

Figure 2:
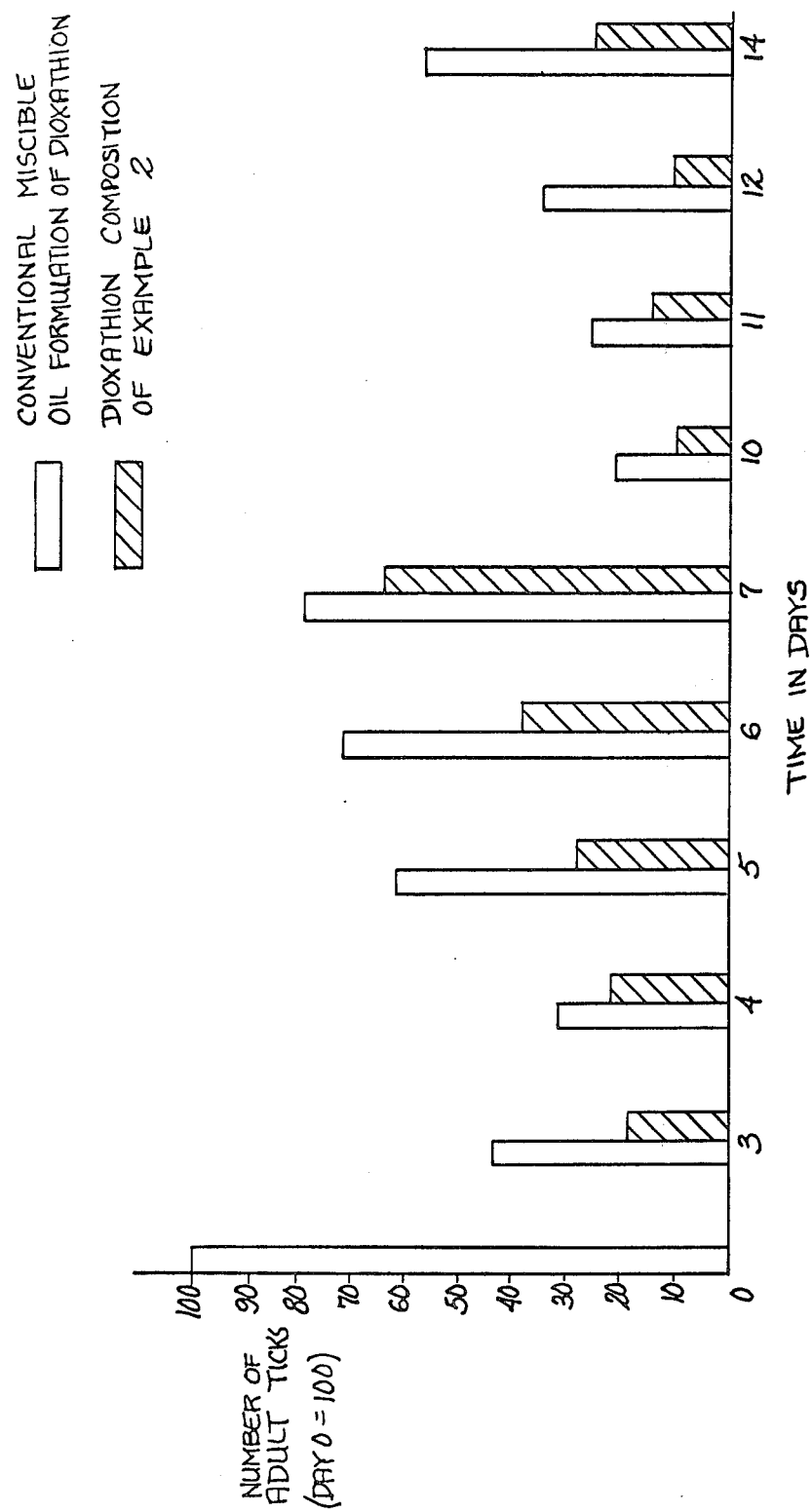
FIG. 2 is a graph showing comparative infestation of ticks in point of time in accordance with the trial tests referred to in Example 7.

The results are represented in FIG. 2, which is a comparative scale, the number of ticks at each count representing a percentage of the number of ticks counted on day 0. These results show that the conventional miscible oil formulation exerted a residual effect until the fourth and the tenth day, but thereafter a steady attachment of ticks took place. On the group treated with the composition of the invention, tick attachment was depressed until the sixth and twelfth day, with the result that successful tick attachment on the seventh day was much less than when the conventional formulation was used. This trial clearly indicates that tick infestations can be controlled and oradicated sooner if the composition of the invention is used instead of the conventional miscible oil formulation.

EXAMPLE 8

Figure 3:
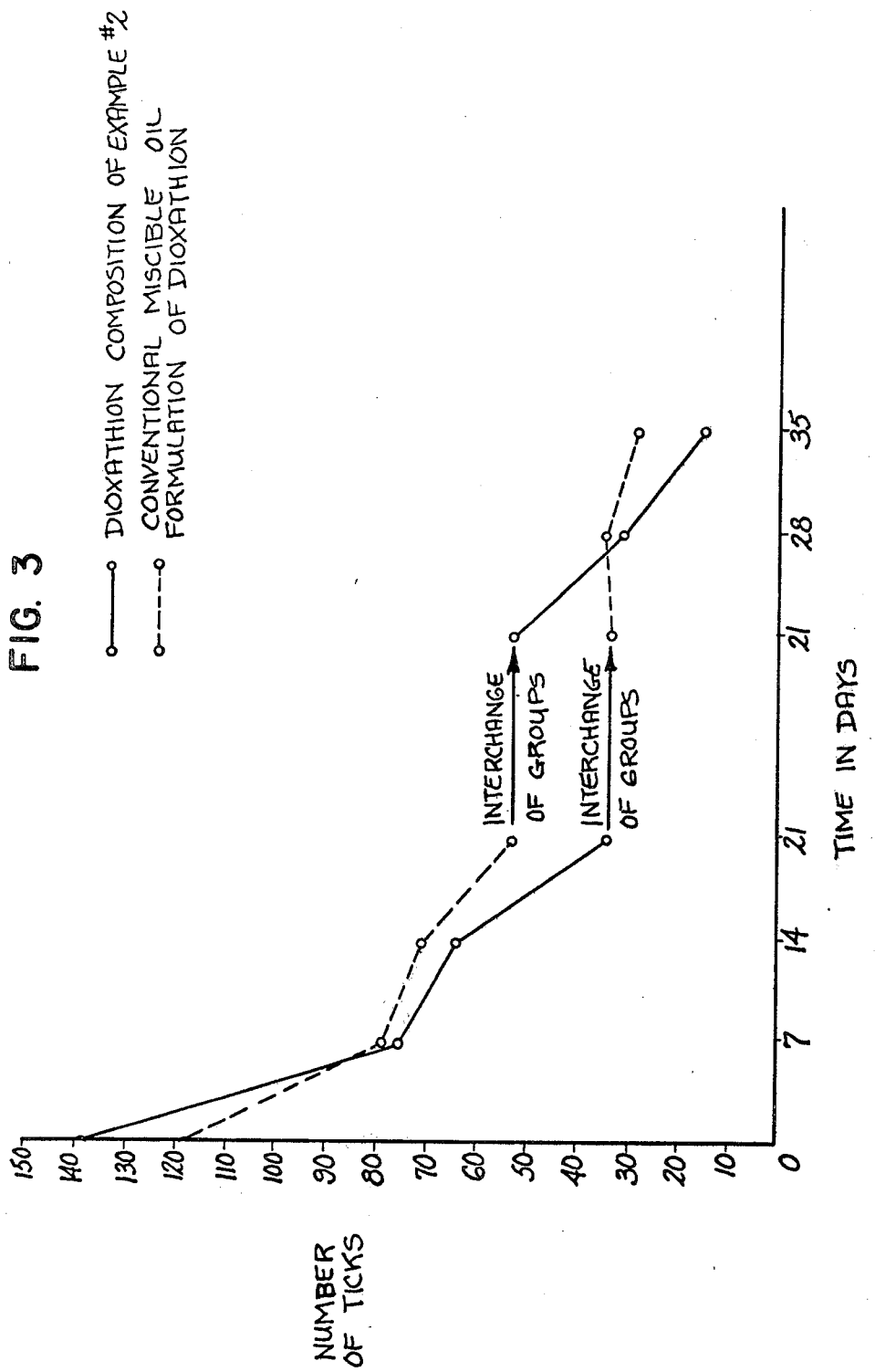
FIG. 3 is a graph showing comparative infestation of ticks in point of time in accordance with the trial tests referred to in Example 8.

This example describes another cooperative field trial with cattle, which was directed to eliminate the possiblity that one group of animals is more succeptible to infestation than another group. The trial was conducted against the same tick as in Example 6 and using the method of Example 6. The same formulation and composition of dioxathion were used, and these were diluted in water to provide a concentration of the active ingredient in each wash of 0.05 percent w/v. The results are repesented in FIG. 3.

The "number of ticks" refers to the number of engorged female ticks on the ears counted before treatment. The treatment group were interchanged after three weekly treatments. These results showed that, after three treatments, the group treated with the composition of the invention was significantly less infested then the group treated with the conventional miscible oil formulation. After count on day 21, the groups interchanged and, after two further treatments, the composition of the present invention again achieved superior results as compared with the conventional miscible oil formulation.

EXAMPLE 9

Laboratory tests to determine the dornal irritancy of compositions of the invention, as compared with conventional miscible oil formulations, were carried out according to a method using rabbits and described by J. W. Draise in "The Appraisal of the Safety of Chemicals in Foods, Drugs and Cosmetics," pp. 46 to 48; Published in 1969 by Association of Food and Drug Officials of the United States of America, Editorial Office, 2411 N. Charles Street, Baltimore, U.S.A.

The compositions and formulations were all diluted to one volume of dip in twenty volumes of water, which gave a higher active ingredient content for the emulsions prepared from compositions of the invention.

The results of those tests are given in Table II. Sample A is the Dioxathion conventional miscible oil formulation, B is the Chlorfenvinphos conventional miscible oil formulation, and C is the mixed Dioxathion/chlorfenvinphos conventional miscible oil formulation, all which are described in Example 5. D is the composition of Example 2, E is the composition of Example 1 and F is the composition of Example 3.

TABLE II

|  |  | Sample | | | | | |
|---|---|---|---|---|---|---|---|
|  |  | A | B | C | D | E | F |
| Non-abraded | Total score | 0 | 2 | 0 | 0 | 0 | 0 |
|  | Average | 0 | 0.3 | 0 | 0 | 0 | 0 |
| Abraded | Total score | 9 | 10 | 11 | 8 | 6 | 3 |
|  | Average | 1.5 | 1.7 | 1.8 | 1.3 | 1.0 | 0.5 |
| Abraded and non-abraded | Total score | 9 | 12 | 11 | 8 | 6 | 3 |
|  | Average | 0.75 | 1.0 | 0.51 | 0.66 | 0.5 | 0.25 |

These results show that on non-abraded skin there is no apparent difference between the compositions and the formulations. On abraded skin the results clearly show the lower irritancy of the compositions of the invention, particularly since the active ingredient content was about three times that of the conventional formulations.

EXAMPLE 10

A field trial was conducted to compare the reactions of cattle to spray washes prepared from the compositions of the invention and the conventional miscible oil formulations presently in use.

Spraying was used since experience has shown that the reactions of cattle to the application of ixodicidal washes can be gauged as well after spraying as after dipping.

The materials used were:

A: the Dioxathion/chlorfenvinphos composition of Example 3

B: the mixed Dioxathion/chlorfenvinphos conventional miscible oil formulation described in Example 5

C: a formulation containing the solvents and emulsifiers of B without active ingredient.

The standard strength spray washes prepared from A and B contained 0.03 percent w/v of active ingredient, while those prepared from C contained the same concentration of the solvents and the emulsifiers as for the spray wash prepared from B.

Eighteen mature Jersey cows in milk were divided into nine groups of two. The groups were hand sprayed with the washes prepared from A, B and C at the standard strength, double strength and four times standard strength.

A panel of three observers was appointed as judges to record the reactions of the cattle to the spray treatments. The comparative test was based on a points system in which Nil indicated no reaction; 3+ indicated pronounced reaction (such as profuse salivation, restlessness, head shaking and foot movement); and 2+ and 1+ indicated intermediate reactions. The judges were unaware of the order of application to the animals of the different spray washes, the contents of the washes, and their strength.

The results of these trials are given in Table III.

TABLE III

| Spray wash and strength | Group | Marks of Judges 1 | 2 | 3 | Accumulative Score |
|---|---|---|---|---|---|
| A-Standard | 1 | Nil | Nil | Nil | Nil |
| B-Standard | 2 | 1 + | Nil | 1 + | 2 + |
| C-Standard | 3 | Nil | Nil | Nil | Nil |
| C-double | 4 | Nil | Nil | Nil | Nil |
| C-four times | 5 | 2 + | 3 + | 3 + | 8 + |
| B-double | 6 | 2 + | 2 + | 2 + | 6 + |
| A-double | 7 | 1 + | Nil | Nil | 1 + |
| A-four times | 8 | Nil | Nil | Nil | Nil |
| B-four times | 9 | 3 + | 3 + | 3 + | 9 + |

These results showed that the spray washes prepared from compositions of the invention has substantially no irritant effect on the cattle, even when used at four times the normally recommended concentration, while those made from the conventional formulations produced substantial irritation.

EXAMPLE 11

A further field trial with cattle was conducted by mechanical spraying methods to determine comparative irritancy, using the materials A, B and C of Example 10 to prepare the spray washes.

The active ingredient concentration of the washes prepared from A and B was 0.04 percent w/v, and the wash prepared from C contained the same amount of solvents and emulsifiers as the wash prepare from 1.

Two observers were appointed as judges to record the reactions of the cattle on the same scoring scale as given in Example 10.

156 Head of cattle were sprayed each time in the same order of herds. The order, in which the formations were sprayed, was B, then C followed by A.

The results are given in Table IV.

TABLE IV

| Spray wash | Marks of the Judges 1 | 2 | Accumulative Score |
|---|---|---|---|
| A | Very slight salivation in 2 animals, with 9 others showing mild salivary dribbles | Very slight salivation in 2 animals, with 7 others showing an occasional dribble | |
| | ½ + | ½ + | 1 + |
| B | Salivation seen in 26 animals 2 + | Salivation seen in 26 animals 2 + | 4 + |
| C | Definite salivation in 3 animals, slight but detectable salivation in 13 others | Definite salivation in 3 animals, slight but detectable salivation in 15 others | |
| | 1 + | 1 + | 2 + |

Again, these results clearly show that the compositions according to the invention have less undesirable effects on cattle than the conventional miscible oil formulations containing solvent. It is significant that the washes made from composition of the invention are even better in this respect than the washes prepared from the material containing no active ingredient but the same amount of solvent as in the conventional miscible oil formulation.

The foregoing Examples show that the use of washes prepared from the compositions of the invention has definite advantages over the use of washes prepared from the conventional miscible oil formulations used at present. Of particular importance are the enhanced biological activity and residual effectiveness of washes. This enhancement will enable farmers to obtain a higher initial kill, to destroy an infestation more rapidly, and to permit a reduction in the number of applications of pesticide in the infective season. This is of major importance in a country beset with ectoparasite control problems, for example cattle ticks, in which any marginal improvement can provide a substantial overall saving in the use of a pesticide.

The reduced irritation of the washes made from compositions of the invention is of practical importance especially in the spraying or dipping of large animals. Irritated animals emerging from a dipping bath or spray race into the draining pens are known to damage or destroy the pens, and injure themselves and adjacent animals, thus also making them more susceptible to infections.

These advantages in the use of washes made from dioxathion and mixed dioxathion/chlorfenuinphos compositions of the invention are surprisingly achieved without any substantial difference in the exhaustion rate of the washes as compared to washes made from conventional miscible oil formulations. Further advantages lie in the compositions themselves, such as the reduction in cost of packaging and transport per unit weight of the active ingredient. Limited experiments with a dioxathion composition of the invention also show that it was not more toxic dermally to mammals than a conventional miscible oil formulation containing a substantially lower concentration of the active ingredient, suggesting that the compositions of the invention are not more dangerous to handle than the conventional formulations. With the elimination of the solvent it is also possible to pack the compositions in plastic containers, for example polythene, which are slowly permeated by the conventional miscible oil formulations at a rate depending upon the nature and thickness of the wall of the container.

In vivo tests with the compositions of the invention and with the conventional miscible formulations have also shown that, with washes of equal concentration of an organo-phosphorous pesticide, there was no significant difference in inhibition of blood cholinesterase activity in sheep and cattle sprayed with the washes. Blood cholinesterase activity is used as a measure of the toxicity of organo-phosphorous compounds, and these tests indicate that the mammalian toxicity of the washes prepared from compositions of the invention were not more toxic than those made from conventional formulations.

Tests by the South African Wool Textile Research Institute, in which wool and mohair were dipped in chlorfenvinphos emulsion washes, also showed that with the compositions of the invention the effects on wool were similar to those with the conventional formulations, except that sample discolouration tended to be slightly less with the compositions of the invention.

EXAMPLE 12

The biological efficiency of chlorofenvinphos/bromophos ethyl composition according the invention was compared with that of a conventional miscible oil formulation containing these pesticides in a field with frikaner cattle grazing on fields heavily infested with *Rhinicephalus appendiculatus* (Brown Ear Tick).

The method used was that described by J. A. F. Baker and G. E. Thompson in the Journal of the South African Veterinary Medical Association, Vol. 37, No. 3. pp. 367–372.

The composition of the chlorofenvinphos/bromophos ethyl composition of the invention was prepared from the following ingredients using the method of Example 1:

| | |
|---|---|
| Chlorfenvinphos (technical grade) | 43.7% w/w |
| Bromophos ethyl (technical grade) | 43.7% w/w |
| Calcium dodecyl benzene sulphonate (anionic emulsifier, technical grade 75% w/w) | 3.8% w/w |
| A non-ionic emulsifier blend (A mixture of polyalkylene glycol ether and a condensate of nonylphenol with 10 to 20 mol. ethylene oxide) | 8.8% w/w |

Two conventional miscible oil formulations were used to make up the wash containing the chlorfenvinphos/bromophos ethyl mixture.

The chlorfenvinphos miscible oil formulation was the same as the one used in Example 5.

The bromophos ethyl miscible oil formulation contained the following ingredients:

| | |
|---|---|
| Bromophos ethyl (technical grade) | 52.3% w/w |
| Calcium dodecyl benzene sulphonate (anionic emulsifier, technical grade 75% w/w) | 3.7% w/w |
| Blend of three non-ionic emulsifiers | 5.0% w/w |
| Organic solvent (containing a high proportion of aromatic hydrocarbons) | 39.0% w/w |

These miscible oil formulations were pre-creamed separately and the pre-creamed materials were added to the spray wash tank to give a wash containing equal quantities of chlorfenvinphos and bromophos ethyl.

The washes prepared from the composition and the formulations contained 0.05% w/v of active ingredients.

Tick counts and assessments both at weekly intervals and on the short term system, were undertaken.

The results of these trials are represented in FIG. 4.

These results show that the counts on animals treated with the composition of the invention are consistantly lower than the counts on the animals treated with the conventional miscible oil formulation.

What we claim is:

1. A method for controlling arthropod ectoparasites of mammals infected with same which comprises contacting said mammals with an emulsion wash consisting of a non-aqueous pesticidal concentrate being substantially free of solvent therefor, and sufficient water to provide a total pesticide compound content of from 0.005 to 0.5 parts by weight per 100 parts by volume of said emulsion wash, wherein said non-aqueous pesticidal concentrate consists of: (a) from 65 to 95% by weight of a liquid pesticide compound or a liquid mixture of a liquid pesticide compound and a solid pesticide compound, said pesticide compound being effective for the control of arthropod ectoparasites of mammals, said liquid pesticide compound being selected from 2-chloro-1-(2,4-dichlorophenyl) vinyl diethyl phosphate; O,O,O'O-tetraethyl S,S'-methylene-diphosphorodithioate; 2,3-p-dioxanedithiol S,S-bis (O,O-diethyl phosphorodithioate); O,O-diethyl-O, 2-isopropyl-4-methyl-6-pyrimidyl phosphorothioate; O,O-diethyl O-2,4-dichlorophenyl phosphorothioate; O,O-diethyl S-(p-chlorophenylthio) methyl phosphorodithioate; O,O-diethyl O-4-bromo-2, 5-dichlorophenyl phosphorothioate; O,O-dimethyl O-(3-methyl-4-nitrophenyl) phosphorothioate; O,O-dimethyl O-1,2-dibromo-2,2-dichloroethyl phosphate; or dimethyl 3-methyl-4-methylthiophenyl phosphorothioate; and (b) an effective amount of at least one emulsifier for effecting emulsification of said pesticide compound in water.

2. A method as in claim 1 wherein the emulsifier is a non-ionic surface active agent, an anionic surface active agent, or a mixture of a non-ionic surface active agent and an anionic surface active agent.

3. The method of claim 1 wherein said solid pesticide compound is selected from O,O-diethyl O-3,5,6-trichloro-2-pyridylphosphorothioate; O,O-dimethyl O-(2,4,5-trichlorophenyl) phosphorothioate; or N-(mercaptomethyl)-phthalimido S-(O,O-dimethyl phosphorodithioate).

4. The method of claim 1 wherein said liquid pesticide compound is selected from 2-chloro-1-(2,4-dichlorophenyl) vinyl diethyl phosphate; 2,3-p-dioxanedithiol S,S-bis (O,O-diethyl phosphorothioate); O,O-diethyl O,4-bromo-2,5-dichlorophenyl phosphorothioate; or O,O-diethyl O-2-isopropyl-4-methyl-6-pyrimidyl phosphorothiate.

5. The method of claim 1 wherein said liquid pesticide compound is selected from O,O,O', O'-tetraethyl S,S'-methylene diphosphorodithioate; or O,O-diethyl O-2,4-dichlorophenyl phosphorothioate.

6. The method of claim 1 wherein only said liquid pesticide compound is utilized in said non-aqueous pesticidal concentrate.

7. The method of claim 1 wherein said emulsion wash further includes about 0.05 to 5% by weight of a suitable stabilizer for organo-phosphorous compounds.

8. The method of claim 7 wherein said stabilizer is selected from propylene oxide, epichlorohydrin or triethanolamine.

* * * * *

UNITED STATES PATENT AND TRADEMARK OFFICE
CERTIFICATE OF CORRECTION

PATENT NO. : 4,195,083

DATED : March 25, 1980

INVENTOR(S) : Hoy et al

It is certified that error appears in the above—identified patent and that said Letters Patent are hereby corrected as shown below:

Column 6, line 17, "Toximal MPS" should read --Toximul MP8--

Column 6, line 24, "MP6" should read --MP8--

Column 7, line 31, "mumbers" should read --numbers--

Column 8, line 62, "0.51" should read --0.91--

Column 10, line 19, "¼+" should read --½+--

Signed and Sealed this

Twelfth Day of August 1980

[SEAL]

Attest:

SIDNEY A. DIAMOND

Attesting Officer

Commissioner of Patents and Trademarks